US006506898B1

(12) United States Patent
Flood et al.

(10) Patent No.: US 6,506,898 B1
(45) Date of Patent: Jan. 14, 2003

(54) PROCESS FOR THE PREPARATION OF 1,3, 5-TRIAZINE CARBAMATES FROM AMINO-1,3,5-TRIAZINES AND ORGANIC CARBONATES

(75) Inventors: Lawrence A. Flood, Norwalk, CT (US); Ram B. Gupta, Bronx, NY (US); Revathi Iyengar, Peekskill, NY (US); David A. Ley, New Canaan, CT (US); Vankatarao K. Pai, Stamford, CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 08/452,636

(22) Filed: May 25, 1995

Related U.S. Application Data

(62) Division of application No. 08/061,905, filed on May 14, 1993, now abandoned.

(51) Int. Cl.[7] ............................................. C07D 251/54
(52) U.S. Cl. ..................... 544/196; 544/197; 544/200; 544/204; 544/205; 544/206; 544/208; 525/176; 525/182; 525/559; 525/375
(58) Field of Search ................................ 544/196, 197, 544/200, 204, 208

(56) References Cited

U.S. PATENT DOCUMENTS

| | | | |
|---|---|---|---|
| 3,642,858 A | 2/1972 | Frevel et al. | 260/463 |
| 4,480,101 A | 10/1984 | Meyer | 544/320 |
| 4,500,655 A | 2/1985 | Brennan | 521/163 |
| 4,565,869 A | 1/1986 | Imfeld et al. | 544/323 |
| 4,579,583 A | 4/1986 | Föry et al. | 71/92 |
| 4,579,584 A | 4/1986 | Meyer et al. | 71/93 |
| 4,732,899 A | 3/1988 | Gehret et al. | 514/245 |
| 4,804,757 A | 2/1989 | Böhner et al. | 544/319 |
| 4,878,938 A | 11/1989 | Hanagan | 71/92 |
| 4,939,213 A | 7/1990 | Jacobs, III et al. | 525/329.9 |
| 4,944,792 A | 7/1990 | Meyer et al. | 71/92 |
| 4,944,793 A | 7/1990 | Meyer et al. | 71/93 |
| 4,944,794 A | 7/1990 | Meyer et al. | 71/93 |
| 5,017,212 A | 5/1991 | Ishida et al. | 71/92 |
| 5,084,541 A | 1/1992 | Jacobs, III et al. | 528/45 |
| 5,091,556 A | 2/1992 | Calderoni et al. | 560/24 |
| 5,103,041 A | 4/1992 | A'Court et al. | 560/132 |
| 5,120,524 A | 6/1992 | Ellgen | 423/588 |
| 5,138,015 A | 8/1992 | Yagii et al. | 528/44 |
| 5,187,306 A | 2/1993 | Tsuboniwa et al. | 560/157 |
| 5,200,547 A | 4/1993 | Riley et al. | 558/265 |
| 5,380,843 A | 1/1995 | Kanda et al. | 544/197 |
| 5,405,959 A | 4/1995 | Gupta | 544/195 |

FOREIGN PATENT DOCUMENTS

| | | |
|---|---|---|
| EP | 0323514 A1 | 7/1988 |
| EP | 0511948 A2 | 11/1992 |
| EP | 0523508 A2 | 1/1993 |
| EP | 0565774 A2 | 10/1993 |
| EP | 0604922 A1 | 7/1994 |
| EP | 0624577 A1 | 11/1994 |
| JP | 3200249 | * 9/1991 ................ 544/204 |
| WO | WO92/06950 | 4/1992 |

OTHER PUBLICATIONS

"Process for 4–Methoxy–N, 6–Dimethyl–1,3, 5–Triazin–2–Amine," Research Disclosure, 27556, Mar. 1987.

"Melamine Derivatives. 18. Reactions of Melamine and Benroguanamine With Ethyl Chlorocarbonate," Chemical Abstracts, 72946d, vol. 82, 1975.

"Carbonylation Reactions. 8. Carbonylation of 1–Propanol and 1–Butano By Carbon Monoxide in the Presence of Copper (II) Chloride," Chemical Abstracts, 41858k, vol. 79, 1973.

"Continuous Manufacture of Alkyl Carbonates," 23–Aliphatics, 3112a, vol. 80, pp. 271, 1974.

"Dialkyl Carbonates from Alkyl Halides," Chemical Abstracts, 203503x, vol. 90, pp. 570, 1979.

"Carbonic Acid Esters," 23–Aliphatics, 149787q, vol. 93, pp. 677, 1980.

"Carbonic Acid Diesters," 23–Aliphatics, 160110j, vol. 103, pp. 669, 1985.

"Continuous Preparation of Diaryl Carbonates from Dialkyl Carbonates," Chemical Abstracts, 60275h, vol. 118, pp. 10, 1993.

"Continuous Process for Manufacturing Dialkyl Carbonates and Diols by Transesterification of Cyclic Carbonates With Alcohols," Chemicals Abstracts, 80498m, vol. 118, pp. 790, 1993.

"Chemistry of Chloroformates," Chem. Rev. 64, Marcus Matzner, Raymond P. Kurkjy and Robert J. Cotter, pp. 645–687, 1964.

"Six–Membered Heterocyclic Isocyanates and Isothiocyanates: Synthesis and Reactions," Synthesis, No. 6, Gerrit L'abbé, pp. 525–588, 1987.

"An Improvement in the Synthesis of Ethyl Pryrimidine Carbamates," J. Heterocyclic Chem., Gilles Auzou and Richard Rips, vol. 18, pp. 835–836, 1981.

"Preparation of Carbonate Diesters," 23–Aliphatics, 168692f, vol. 118, 1993.

"Preparation of Dialkyl Carbonates via the Phase–Transfer–Catalyzed Alkylation of Alkali Metal Carbonate and Bicarbonate Salts," J. Org. Chem., James A. Cella and Sidney W. Bacon, 49, pp. 1122–1125, 1984.

(List continued on next page.)

Primary Examiner—Richard L. Raymond
(74) Attorney, Agent, or Firm—James A. Jubinsky; Valerie T. Didamo; Claire M. Schultz

(57) ABSTRACT

Provided is a process for preparing an at least bis-carbamate functional 1,3,5-triazine by contacting an at least diamino-1,3,5-triazine, an acyclic organic carbonate and a base, as well as certain novel compositions producible thereby. Also provided are substantially halogen contamination free crosslinker compositions comprising the products obtainable by the process, and curable compositions based upon these crosslinkers.

32 Claims, No Drawings

OTHER PUBLICATIONS

"A New Synthesis of Carbonates. The Reaction of Carbon Monoxide With Alkolates in the Presence of Selenium," Tetrahedron Letters No. 51, Kiyoshi Kondo, Noboru Sonoda and Shigeru Tsutsumi, pp. 4885–4886, 1971.

"Phasentransfer–katalytische Herstellung von Kohlensäureestern ohne Verwendung von Phosgen," Chem. Ber., M. Lissei und E.V. Dehmlow, vol. 114, pp. 1210–1215, 1981.

"Triazine Isocyanates Part I: 2,4–diphenyl–s–triazine–6–isocyanate," Recueil, E.F.J. Duynstee, vol. 80, pp. 563–571, 1961.

"Triazine Isocyanates Part II: Reaction of 2,4–diamino–s–triazines with ethyl chlorocarbonate," Recueil, E.F.J. Duynstee and TH. Veerkamp, vol. 81, pp. 241–254, 1962.

"The Chemistry of Melamine," American Cyanamid Company, pp. 1–51. 1954.

"s–Trianzines and Derivatives," The Chemistry of Heterocyclic Compounds, Edwin M. Smolin and Lorence Rapport, pp. 218–388, 1959.

"The Pyrimidines," The Chemistry of Heterocyclic Compounds, D.J. Brown, pp. 336–339 & 320–322, 1962.

European Search Report No. EP 941074916., (1994).

28–Heterocyclic Compounds, Chemical Abstracts, 88585b, vol. 75, (13), pp. 363–364, 1971.

* cited by examiner

PROCESS FOR THE PREPARATION OF 1,3, 5-TRIAZINE CARBAMATES FROM AMINO-1,3,5-TRIAZINES AND ORGANIC CARBONATES

This application is a divisional of U.S. application Ser. No. 08/061,905, filed May 14, 1993, now abandoned.

BACKGROUND OF THE INVENTION

1. Field of the Invention

This invention relates to the preparation of at least bis-carbamate functional 1,3,5-triazines from amino-1,3,5-triazines and organic carbonates in the presence of a base, as well as to certain novel carbamates producible thereby.

2. Description of Related Art

Various derivatives of amino-1,3,5-triazines are described in the literature as being utilized in a wide variety of fields. An important use of certain of these derivatives, such as the methoxymethyl derivatives of melamine and guanamines, is as crosslinkers and/or reactive modifiers in curable compositions based upon active hydrogen groups-containing resins. While these methoxymethyl derivatives provide excellent results in a number of aspects, one disadvantage to their use is that, under curing conditions, formaldehyde is released as a volatile by-product. It has, therefore, been a desire of industry to find an acceptable alternative for these well-known amino-1,3,5-triazine derivatives which do not emit formaldehyde upon cure.

One such alternative which has shown great promise is the carbamate functional 1,3,5-triazines which are disclosed in commonly owned U.S. Pat. Nos. 4,939,213, 5,084,541, U.S. application Ser. No. 07/968,871 (filed Oct. 30, 1992, which is a continuation-in-part of U.S. application Ser. No. 07/793,077, filed Nov. 15, 1991 and now abandoned), and U.S. application Ser. No. 07/998,313 (filed Dec. 29, 1992), all of which are hereby incorporated by reference as if fully set forth. Specifically, the carbamate functional 1,3,5-triazines disclosed in these references have been found to be particularly useful as crosslinkers in coating compositions based upon hydroxy functional resins, with the cured coatings possessing a wide range of desirable film and resistance properties.

One hinderance to the commercial use of these carbamate functional 1,3,5-triazines has been that the known preparation methods can be somewhat cumbersome, difficult and expensive. For example, in previously mentioned U.S. Pat. Nos. 4,939,213 and 5,084,541, the 1,3,5-triazine carbamates are produced in a two-step process by first reacting an amino-1,3,5-triazine with oxalyl chloride to produce an isocyanate functional intermediate, then reacting this intermediate with an alcohol. The primary disadvantages to this process include the use of a halogenated starting material, the handling of an isocyanate functional intermediate, the production of halogenated by-products and the low ultimate yield of the desired carbamate functional product.

Further, in previously mentioned U.S. application Ser. No. 07/968,671, the carbamate functional 1,3,5-triazines are produced in a one-step process by reacting a haloaminotriazine with an acid halide. The primary disadvantages to this process include the use of halogenated starting materials and the production of halogenated by-products.

It has now been surprisingly discovered after extensive research that at least bis-carbamate functional 1,3,5-triazines can be readily produced with high selectivity and in excellent yields by the reaction of (a) at least diamino-1,3,5-triazines and (b) acyclic organic carbonates in the presence of relatively strong bases.

It should be noted that it is generically known to obtain carbamates via the reaction of amines with carbonates. It is, however, well-known to those of ordinary skill in the art that the amine functionality of amino-1,3,5-triazines (such as the amine functionality of melamines and guanamines) is not equivalent to the other types of typical amine functionality. Indeed, melamines and guanamines are among the least reactive of the "amines" and the most difficult to functionalize, and their behavior cannot normally be correlated to that of other known amines, even structurally similar amines such as pyrimidines.

For example, most "typical" amines are highly reactive with acid halides. In a publication by E. M. Smolin and L. Rapaport entitled "S-Triazines and Derivatives," Interscience Publishers Inc., New York, page 333 (1959), however, it is reported that attempts to react an acid halide with the amino group on a 1,3,5-triazine such as melamine have not been successful.

Further, attempts to functionalize amino-1,3,5-triazines often results in substitution at the nitrogen on the triazine ring. For example, it is known that the reaction of melamine with alkyl halides, such as allyl chloride, results in alkyl substitution at the nitrogen on the triazine ring resulting in isomelamine derivatives.

To date, a disclosure has not been found whereby an at least bis-carbamate functional 1,3,5-triazine has been prepared from an at least diamino-1,3,5-triazine and an organic carbonate. While several references appear to generically disclose (among other techniques) that mono-carbamate 1,3,5-triazines can be prepared by the reaction of a mono-amino 1,3,5-triazine and an organic carbonate (see U.S. Pat. Nos. 5,017,212, 4,579,583, 4,878,938, 4,480,101, and 4,804,757, and PCT Unexamined Application No. 9206965), no specific example could be found in these references of any mono-carbamate 1,3,5-triazine actually having been so prepared. The only disclosure found exemplifying a mono-carbamate 1,3,5-triazine produced from a monoamino-1,3,5-triazine and an organic carbonate is in Research Disclosure, Vol. 275, p. 162 (1987).

Quite relevant to the surprising nature of the present invention is an unsuccessful attempt to prepare a 1,3,5-triazine-2,4,6-tris-carbamate from an amino triazine and ethyl chloroformate (a potential precursor component of an organic carbonate), which is reported in an article by H. Kitajima et al in Yuki Gosei Kagaku Kyokai Shi, Volume 32, Number 9, page 723–26 (1974) (Chemical Abstracts, Volume 82, Number 11:72946). Instead of producing the desired tris-carbamate, the authors reported the formation of an imide via diacylation of the amino groups. Similarly, the reaction of benzoguanamine with ethyl chloroformate produces N,N-diethoxycarbonyl benzoguanamine. Such imide functional compounds are unsuitable as crosslinking agents. Similar results are also reported in Rec. Trav. Chim., Vol. 81, pages 241–254 (1962).

In fact, it is clearly surprising in light of the state of the art that at least bis-functional carbamate derivatives can be produced with high selectivity and yield from the at least diamino-1,3,5-triazines via the present inventive process, as described in detail below.

SUMMARY OF THE INVENTION

As indicated above, the present invention includes a process for preparing an at least bis-carbamate functional 1,3,5-triazine by contacting, at a temperature and for a length of time sufficient to produce the at least bis-carbamate functional 1,3,5-triazine, a mixture comprising:

(a) an at least diamino-1,3,5-triazine represented by the formula:

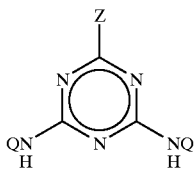

wherein Z is selected from the group consisting of hydrogen, hydrocarbyl, a group represented by the formula NHQ, and a group represented by the formula:

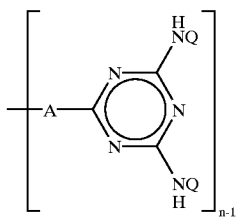

wherein
A is an n-functional anchor,
n is at least 2, and
each Q is independently selected from the group consisting of hydrogen, a hydrocarbyl and a hydrocarbyloxy hydrocarbyl, with the proviso that at least two of the Q groups are hydrogen;

(b) an acyclic organic carbonate; and
(c) a base.

As indicated above, the advantages of the present process include, for example:

(1) the present process does not require handling of an isocyanate intermediate;
(2) the present process can be utilized without corrosive halogenated starting materials and without the production of halogenated by-products;
(3) each amino nitrogen of the amino 1,3,5-triazine starting material is substituted only once, producing at least bis-carbamate functional 1,3,5-triazines capable of use as crosslinking agents; and
(4) the desired at least bis-carbamate 1,3,5-triazines can readily be produced with high selectivity and in excellent yields.

In addition, the present process allows the production of certain novel at least bis-carbamate 1,3,5-triazines which also form a part of the present invention. A first class of these novel at least bis-carbamate 1,3,5-triazines have the following general formula:

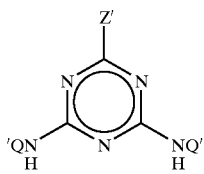

wherein Z' is selected from the group consisting of hydrogen, hydrocarbyl, a group represented by the formula NHQ', and a group represented by the formula:

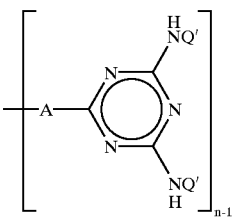

wherein
A is an n-functional anchor,
n is at least 2,
each Q' is independently selected from the group consisting of a hydrocarbyl, a hydrocarbyloxy hydrocarbyl and a group represented by the formula COOY, with the proviso that at least two of the Q' groups are COOY, and
each Y is independently selected from the group consisting of a hydrocarbyl group and a hydrocarbyloxy hydrocarbyl ether group, with the proviso that at least one Y group is a hydrocarbyloxy hydrocarbyl ether group.

A second class of these novel at least bis-carbamate functional 1,3,5-triazines also have the above general formula, wherein Z' is selected from the group consisting of a group represented by the formula NHQ', and a group represented by the formula:

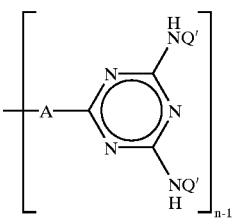

wherein
A is an n-functional anchor,
n is at least 2,
each Q' is independently selected from the group consisting of a hydrocarbyl, a hydrocarbyloxy hydrocarbyl and a group represented by the formula COOY, with the proviso that (i) at least two of the Q' groups are COOY and (ii) at least one of the Q' groups is other than COOY, and
each Y is independently a hydrocarbyl group or a hydrocarbyloxy hydrocarbyl ether group.

Another important aspect of the present invention is that the process can be conducted under substantially halogen free conditions; consequently, the resulting products can be made substantially free of halogen contamination (and particularly chlorine). In other words, it is possible via the use of the present process to provide substantially halogen-free crosslinker compositions comprising the at least bis-carbamate functional 1,3,5-triazines, and to formulate curable compositions comprising these halogen free crosslinker compositions.

These and other features and advantages of the present invention will be more readily understood by those of ordinary skill in the art from a reading of the following detailed description.

DETAILED DESCRIPTION OF THE PREFERRED EMBODIMENTS

The Amino-1,3,5-triazine

As indicated above, the amino-1,3,5-triazines suitable for use in the present invention include those represented by the formula:

wherein Z is selected from the group consisting of hydrogen, hydrocarbyl, a group represented by the formula NHQ, and a group represented by the formula:

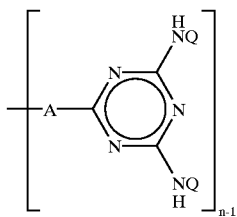

wherein

A is an n-functional anchor, n is at least 2, and each Q is independently selected from the group consisting of hydrogen, a hydrocarbyl and a hydrocarbyloxy hydrocarbyl, with the proviso that at least two of the Q groups are hydrogen.

The term "hydrocarbyl" in the context of the invention is defined as a group which contains exclusively carbon and hydrogen atoms and includes, for example, alkyl, aryl, aralkyl, alkenyl, and substituted derivatives thereof.

The term "amino-1,3,5-triazine" in the context of the invention refers to derivatives of 4-substituted-2,6-diamino-1,3,5-triazines and 2,4,6-triamino-1,3,5-triazines. The term "amino-1,3,5-triazine" does not, however, include monoamino-1,3,5-triazines which, being monofunctional, are incapable of producing at least bis-carbamate functional 1,3,5-triazines suitable for use as crosslinking agents.

The group A in the above formula is an n-functional anchor which can, for example, be a hydrocarbon residue, an amino compound residue, oxygen or sulfur. More preferably, the amino-1,3,5-triazines including the group A have the following general formula

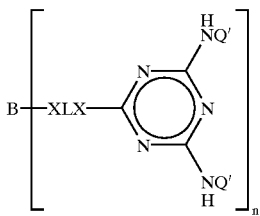

wherein

B is selected from the group consisting of a hydrocarbyl and a hydrocarbyloxy hydrocarbyl, each X is independently selected from the group consisting of NH, NL, $CH_2$, O, S and $CO_2$, L is selected from a hydrocarbyl and a hydrocarbyloxy hydrocarbyl, n is at least 2, and Q' is as defined above.

The preferred 4-substituted-2,6-diamino-1,3,5-triazines are those represented by the above general formula wherein Z is selected from the group consisting of hydrogen and a hydrocarbyl, and more prefereably from the group consisting of an alkyl of 1 to 20 carbon atoms, alkenyl of 3 to 20 carbon atoms, aryl of 6 to 20 carbon atoms, and aralkyl of 7 to 20 carbon atoms. Most preferably, the 4-substituted-2, 6-diamino-1,3,5-triazines are guanamines such as acetoguanamine, ethyl carboguanamine, propyl carboguanamine, butyl carboguanamine, cyclohexyl carboguanamine and benzoguanamine.

The preferred 2,4,6-triamino-1,3,5-triazines are those represented by the above general formula wherein Z is NHQ. Most preferred are those wherein all Q groups are hydrogen, that is, melamine.

The Acyclic Organic Carbonate

A wide variety of acyclic organic carbonates are suitable for use in the process of the present invention. The term "acyclic" in the context of the invention is meant to exclude the cyclic carbonates such as alkylene carbonates (for example ethylene carbonate), but specifically include other carbonates containing cyclic functionality such as those described below.

In preferred embodiments, the acyclic organic carbonates are represented by the formula:

$$R^1(CO_3)R^2$$

wherein $R^1$ and $R^2$ are independently selected from a hydrocarbyl group and a hydrocarbyloxy hydrocarbyl ether group. As hydrocarbyl groups may be mentioned aryl, alkyl, aralkyl and alkenyl groups. As hydrocarbyloxy hydrocarbyl ether groups may be mention alkoxy alkyl ether and alkoxy aryl ether groups. Preferred among the acyclic organic carbonates are diaryl carbonates, dialkyl carbonates, aryl alkyl carbonates and dialkenyl carbonates.

As examples of diaryl carbonates may be mentioned those wherein each of $R^1$ and $R^2$ in the above formula is independently an aryl group of 6 to 20 carbon atoms. Specific examples include diphenyl carbonate, di-(para-tolyl) carbonate, di-(para-chlorophenyl) carbonate, di-(pentachlorophenyl) carbonate, di-(alpha-naphthyl) carbonate, di-(beta-naphthyl) carbonate, and mixed diaryl carbonates such as phenyl para-chlorophenyl carbonate and the like.

As examples of dialkyl carbonates may be mentioned those wherein each of $R^1$ and $R^2$ in the above formula is independently an alkyl group of 1 to 20 carbon atoms, and preferably 1 to 4 atoms. Specific examples of such dialkyl carbonates include dimethyl carbonate, diethyl carbonate, dipropyl carbonate, dibutyl carbonate, methyl butyl carbonate, and the like.

As examples of aryl alkyl carbonates may be mentioned those wherein one $R^1$ and $R^2$ in the above formula is an aryl group as defined above, and the other is an alkyl group as also defined above. Specific examples of such aryl alkyl carbonates include methyl phenyl carbonate and butyl phenyl carbonate.

As examples of dialkenyl carbonates may be mentioned those wherein each of $R^1$ and $R^2$ in the above formula is independently an alkenyl group of 3 to 20 carbon atoms. A specific example of such a dialkenyl carbonate is diallyl carbonate.

Especially preferred of the above include dimethyl carbonate, diethyl carbonate, dibutyl carbonate, methyl butyl carbonate, diphenyl carbonate and mixtures thereof.

A large number of these organic carbonates are generally commercially available and usable as such. They may also by prepared by methods well known in the art including the following:

(a) alkylation of alkali metal carbonates with alkyl halides, disclosed in JP 55-038,327; Chem. Abstr. 93 (15):149787 Q; JP-54-014,920; Chem Abstr. 90(25) :203503 X; Chem. Berichte, vol. 114, 1210–1215 (1981); and J. Org. Chem. vol. 49 (6) 1122–1125 (1984).

(b) exchange reactions of carbonates with alcohols, disclosed in U.S. Pat. No. 3,642,858; JP 04-198,141; Chem. Abstr. 118(5): 80498m; and WO 92-18,458.

(c) reaction of an alcohol with phosgene via the intermediacy of a haloformate, disclosed in Chem. Reviews, Vol. 64, pages 645–687 (1964); FR 2,163,884; and Chem. Abstr. 80(1):3112a.

(d) carbonylation of alcohols with carbon monoxide in the presence of copper (II) salts, selenium, or palladium (II) compounds disclosed respectively in Izv. Akad. Nauk SSSR, Ser. Org. Khim., No. 4, pages 804–6 (1973); Chem. Abstr. 79(7):41858k; Tetrahedron Letters, No. 51, pages 4885–6 (1971); and U.S. Pat. No. 5,120,524.

(e) carbonylation of alkyl nitrites with carbon monoxide in the presence of platinum (II) and palladium (II) salts, disclosed in JP 60-09493; Chem. Abstr. 103(19) :160110j; EP-A-523,508; Chem. Abstr. 118: 147169g; JP04-290,849; and Chem. Abstr. 118:168692f.

(f) reaction of an alcohol with carbon dioxide and selected hydrocarbyl halides in the presence of nitrogen-containing bases, disclosed in EP-A-511948; and U.S. Pat. No. 5,200,547.

All of the above-mentioned references are incorporated by reference herein as if fully set forth.

In the process of the invention, any of the methods described above may be used to prepare an organic carbonate in situ for reaction with an amino-1,3,5-triazine. Thus, for example, dibutyl carbonate or methyl butyl carbonate or a mixture thereof may be prepared by contacting dimethyl carbonate with butanol (i) in the presence of a base, and thereafter contacting the resulting mixture with an amino-1,3,5-triazine, or (ii) in the presence of both the base and the amino-1,3,5-triazine, to produce an at least bis-carbamate functional 1,3,5-triazine in accordance with the process of this invention.

The Base

In the practice of the invention, a relatively strong base is used. It is preferred that such base be of sufficient strength to deprotonate the amino groups (Q=H) of the chosen amino-1,3,5-triazine on reaction with the organic carbonate. Without being bound by any structure or theory, it is believed that bases which are capable of deprotonating these amino groups are more effective in accelerating the rate of reaction of the amino-1,3,5-triazine with the organic carbonate than bases which do not readily do so. Based upon the choice of starting amino-1,3,5-triazine, one of ordinary skill in the art will readily be able to determine which bases are capable of so-deprotonating the amino groups of the amino-1,3,5-triazines.

As preferred examples of suitable bases may be mentioned alkali metal hydrides, alkali metal alkoxides, alkali metal hydroxides, alkali metal oxides, alkali metal carbonates, quaternary ammonium alkoxides, quaternary ammonium hydroxides, quaternary phosphonium alkoxides, quaternary phosphonium hydroxides, tertiary amines and mixtures thereof. Sodium and potassium alkoxides are most preferred, and include linear, branched and cyclic alkyl group containing alkoxides and mixtures thereof.

Specific examples of the preferred bases include sodium hydride, potassium hydride, sodium butoxide, potassium butoxide, sodium methoxide, potassium methoxide, sodium ethoxide, potassium ethoxide, sodium propoxide, potassium propoxide, sodium beta-hydroxyethoxide, potassium beta-hydroxyethoxide, sodium hydroxide, potassium hydroxide, sodium oxide, potassium oxide, sodium carbonate, potassium carbonate, benzyl trimethylammonium methoxide, benzyl trimethylammonium hydroxide, methyl triphenylphosphonium methoxide, triphenylphosphonium hydroxide, triethylamine, N-methyl-di-isopropylamine, tri-n-butylamine, tri-n-octylamine, 1,4-diazabicyclo(2.2.2) octane (DABCO), 1,5-diazabicyclo(4.3.0)non-5-ene(DBN), 1,8-diazabicyclo(5.4.0)undec-7-ene(DBU), N-methylpyrrolidine, N-methylpiperidine, N-methylmorpholine, N,N-dimethylpiperazine, pentamethyl guanidine, 2,6-lutidine, 2,4,6-collidine and mixtures thereof.

It is also preferred that the base does not destroy the organic carbonate at a rate sufficiently high to compete with the reaction of the carbonate with the amino-1,3,5-triazine. In cases where the organic carbonate may be partially destroyed by the base, the use of excess amounts of the organic carbonate ensures a high conversion to the carbamate.

Process Conditions

In the process of the present invention, the amino-1,3,5-triazine, organic carbonate and base are contacted at a temperature and a length of time sufficient to produce the desired at least bis-carbamate functional 1,3,5-triazine.

The components are preferably contacted at temperatures in the range of from about 0° C. to about 150° C., and more preferably in the range of from about 25° C. to about 100° C. At these temperatures and depending upon the starting components, substantially complete conversion has been found to occur in a period of time ranging from about ten minutes to about ten hours. After completion of the reaction, the resulting mixture is neutralized with, for example, a mineral acid such as phosphoric acid, sulfuric acid and/or hydrochloric acid. Organic acids and ion exchange resins may optionally be utilized for the neutralization.

The resulting at least bis-carbamate functional 1,3,5-triazine can be recovered from the reaction by, for example, first extracting with an organic solvent, and thereafter either evaporating the solvent or precipitating the product by addition of a nonsolvent.

The contacting of the components of the reaction mixture may be simultaneous or sequential. When simultaneous, contacting is carried out by adding all components of the mixture to the reaction zone at the same time or premixing them prior to the addition, and thereafter allowing the components of the mixture to react at the desired temperature. When sequential, either of the following three procedures can be envisioned:

(i) the amino-1,3,5-triazine and the base are first contacted and, thereafter, the organic carbonate is contacted;

(ii) the organic carbonate and the base are first contacted and, thereafter, the amino-1,3,5-triazine is contacted; and (iii) the amino-1,3,5-triazine and the organic carbonate are first contacted and, thereafter, the base is contacted.

When the organic carbonate and the base are contacted, an exchange between the base and the organic carbonate may take place prior to reaction with the amino-1,3,5-triazine. For example, when dimethyl carbonate and sodium butoxide are contacted, an alkoxy exchange reaction may take place to give, depending on the relative amount of the alkoxide, dibutyl carbonate, methyl butyl carbonate or a mixture thereof. The organic carbonates formed in situ in this manner are usable in the process of the invention, as are organic carbonates prepared in situ by any of the methods of preparation of organic carbonates described hereinabove in section entitled "THE ORGANIC CARBONATE". A base catalyzed exchange between the carbonate and an appropriate solvent (such as an alcohol or hydroxyether solvent) may additionally take place. Most importantly, an exchange between the carbamate product and the base or solvent may also take place, particularly when contacting is carried out over a longer period of time.

The reaction may be carried out in a reaction medium to obtain uniform reaction. The reaction may be carried out either as a homogeneous solution or as a slurry. A reactant or a mixture of reactants may also serve as the reaction medium, particularly if used in excess quantities. The reaction medium typically is a solvent for the reactants, and includes organic solvents such as alcohol, ether, N,N-dialkylformamide, amide and hydrocarbon solvents, as well as mixtures thereof. Alcohol solvents are preferred and include methanol, ethanol, propanol, butanol, pentanol, hexanol, ethylene glycol, 1,2-propylene glycol, 1,3-propylene glycol, 1,4-butylene glycol, 2,3-butylene glycol, isomers thereof as well as mixtures thereof. Ether solvents are also preferred and include, for example, dialkyl ethers, tetrahydrofuran, dioxane and glycol diethers. It is preferred to run the reaction in the substantial absence of water, although the presence of some water may be tolerated.

The amounts of the various ingredients usable in the process of the invention depends on the number of —$NH_2$ groups present in the amino-1,3,5-triazine. At least one equivalent of the organic carbonate per —$NH_2$ group is required to completely convert the —$NH_2$ groups to carbamate functionality; however, more than an equivalent is preferred to ensure high conversion. The amount of base required for reaction is at least a third of an equivalent per —$NH_2$. Preferably, however, at least one equivalent, and more preferably greater than one equivalent, is used to ensure high conversion.

The 1,3,5-triazine Carbamates

This invention provides a process for preparing both known and novel at least bis-carbamate functional 1,3,5-triazines. Generically, these at least bis-carbamate functional 1,3,5-triazines which may be prepared by the process of this invention are represented by the general formula:

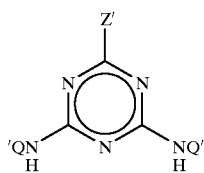

wherein Z' is selected from the group consisting of hydrogen, hydrocarbyl, a group represented by the formula NHQ', and a group represented by the formula

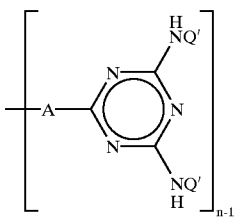

wherein
A is an n-functional anchor,
n is at least 2,
each Q' is independently selected from the group consisting of a hydrocarbyl, a hydrocarbyloxy hydrocarbyl and a group represented by the formula COOY, with the proviso that a least two of the Q' groups are COOY, and
each Y is independently a hydrocarbyl group or a hydrocarbyloxy hydrocarbyl ether group.

Among the novel at least bis-carbamate functional 1,3,5-triazines include, for example, those of the above general formula (I) wherein Z' is selected from the group consisting of hydrogen, hydrocarbyl, a group represented by the formula NHQ', and a group represented by the formula:

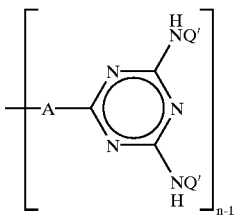

wherein
A is an n-functional anchor,
n is at least 2,
each Q' is independently selected from the group consisting of a hydrocarbyl, a hydrocarbyloxy hydrocarbyl and a group represented by the formula COOY, with the proviso that at least two of the Q' groups are COOY, and
each Y is independently selected from the group consisting of a hydrocarbyl group and a hydrocarbyloxy hydrocarbyl ether group, with the proviso that at least one Y group is a hydrocarbyloxy hydrocarbyl ether group; and (II) wherein Z' is selected from the group consisting of a group represented by the formula NHQ', and a group represented by the formula:

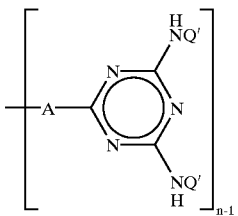

wherein
A is an n-functional anchor,
n is at least 2, each Q' is independently selected from the group consisting of a hydrocarbyl, a hydrocarbyloxy hydrocarbyl and a group represented by the formula COOY, with the proviso that (i) at least two of the Q' groups are COOY and (ii) at least one of the Q' groups is other than COOY, and each Y is independently a hydrocarbyl group or a hydrocarbyloxy hydrocarbyl ether group.

One group of preferred compounds are those wherein each Y is independently a hydrocarbyl group selected from an alkyl of 1 to 20 carbon atoms, alkenyl of 3 to 20 carbon atoms, aryl of 6 to 20 carbon atoms, and aralkyl of 7 to 20 carbon atoms.

Another group of preferred compounds are those wherein each Y is independently a hydrocarbyloxy hydrocarbyl ether group with both hydrocarbyl portions thereof being selected from an alkyl of 1 to 20 carbon atoms, alkenyl of 3 to 20 carbon atoms, aryl of 6 to 20 carbon atoms, and aralkyl of 7 to 20 carbon atoms.

Yet another preferred group of compounds are those wherein at least one Y group is a hydrocarbyl as defined above, and at least one Y group is a hydrocarbyloxy hydrocarbyl ether group as also defined above.

As indicated earlier, the at least bis-carbamate functional 1,3,5-triazines which can be made according to the present invention have utility, for example, as crosslinking agents for hydroxy functional and amino functional resins in curable compositions such as coatings and adhesive compositions. Curable compositions based upon carbamate functional 1,3,5-triazines are discussed in detail in a number of the previously incorporated references.

An important advantage of the present process is that the resulting products can be made free of halogens (and particularly chlorine). In other words, it is possible via the use of the present process to provide halogen contamination free crosslinker compositions comprising the at least bis-carbamate functional 1,3,5-triazines, and to formulate curable compositions comprising these halogen contamination free crosslinker compositions and compositions reactive therewith.

The following examples illustrate various embodiments of the invention.

EXAMPLE 1

A slurry of melamine (0.6217 g, 0.005 mol) and dry dibutyl carbonate (3.46 g, 0.02 mol) was heated to 90° C. under a dry argon blanket. A 20% solution of sodium n-butoxide in butanol (9.72 g, 0.02 mol of sodium n-butoxide) was added to the slurry. The temperature was maintained at 90° C. for 2 hours. At the end of the two hour period, the mixture was cooled and poured into a methylene chloride (50 ml)/2N sulfuric acid (25 ml) mixture. The methylene chloride layer was washed with a saturated sodium chloride solution, dried over magnesium sulfate and concentrated under reduced pressure to yield 1.74 g (82.8%) of a product, whose structure was confirmed by $^1$H NMR to be 2,4,6-tris-butoxycarbonylamino-1,3,5-triazine.

EXAMPLE 2

A slurry of melamine (0.6179 g, 0.0049 mol) and dry dimethyl carbonate (5.22 g, 0.058 mol) was heated to 90° C. under a dry argon blanket. A 20% solution of sodium methoxide in methanol (11.83 g, 0.055 mol of sodium methoxide) was added to the slurry. The heating was continued for 2 hours. At the end of the two hour period, the reaction was allowed to cool and acidified with phosphoric acid. Solid thus obtained was filtered and washed with water until free of acid producing 0.95 g (65%) of a product identified by $^1$H NMR to be 2,4,6-tris-methoxycarbonylamino-1,3,5-triazine.

EXAMPLE 3

1 g of 95% sodium hydride was placed in a two-neck flask equipped with a magnetic stirring bar, a reflux condenser with an argon inlet and a rubber septum. To it was added 40 ml of dimethylformamide (DMF) followed by 1.26 g of melamine. The contents were stirred at room temperature for 15 minutes and then 8.56 g of diphenyl carbonate was added to the flask. The reaction mixture was stirred at room temperature for 4 hours and then poured, with stirring, into 500 ml of 5% aq HCl. A white precipitate was formed which was filtered, washed with water, and dried under reduced pressure to give 4.4 g of crude 2,4,6-tris-phenoxycarbonylamino-1,3,5-triazine. The structure was confirmed by thin layer chromatography (TLC), $^1$H NMR and mass spectroscopy.

EXAMPLE 4

1.0 g of 95% sodium hydride was placed in a two-neck flask equipped with a reflux condenser with an argon inlet, a magnetic stirring bar and a rubber septum. To it was added 40 ml of DMF followed by 1.26 g of melamine. The contents were stirred at room temperature for 15 minutes and then 5.7 ml of diallyl carbonate was added to the flask. The reaction mixture was stirred at room temperature for about 3 hours, and then poured with stirring into 500 ml of ice cold 5% aq. HCl. It was extracted with $CH_2Cl_2$ (2×300 ml) and combined organic extracts washed with water (2×150 ml), dried over anhyd. $Na_2SO_4$ and the solvent was removed under reduced pressure to give 3.75 g of a product identified by $^1$H NMR and mass spectroscopy to be 2,4,6-tris-allyloxycarbonylamino-1,3,5-triazine.

EXAMPLE 5

1.87 g of benzoguanamine was placed in a two-neck flask equipped with a magnetic stirring bar, a rubber septum, and a reflux condenser with an argon inlet. To it was added 3.5 g of dibutylcarbonate and the mixture heated in an oil bath at 90° C. A solution of 12.0 g of 20% sodium butoxide in n-butanol was then added to the reaction flask. After 5 minutes of heating, an almost clear solution was obtained. The reaction mixture was heated for about 30 minutes and then allowed to cool at room temperature. It was then poured into ice-cold 100 ml of 5% aq. Hcl with stirring. The reaction mixture was extracted with $CH_2Cl_2$ (2×60 ml). The combined organic layer was washed with water (2×25 ml), dried over anhydrous $Na_2SO_4$ and filtered. The filtrate was concentrated to dryness under reduced pressure to give 3.95 g of crude product. TLC analysis of the crude product showed the presence of a major and a minor product. The major product was identified by $^1$H NMR and mass spectroscopy to be N,N'-bis-butoxycarbonylbenzoguanamine. The minor product was the mono-carbamate.

EXAMPLE 6

A mixture of 1.25 g of acetoguanamine, 3.5 g of dibutyl carbonate, and 12.0 g of 20% sodium butoxide in n-butanol was heated at 90° C. for 30 minutes. The reaction mixture was treated with ice-cold Hcl (5%) and extracted with $CH_2Cl_2$ (2×60 ml). The combined organic layer was washed with water (2×25 ml), dried ($Na_2SO_4$) and filtered. Removal of solvent under reduced pressure gave 3.2 g of crude N,N'-bis-butoxycarbonylacetoguanamine. The structure was confirmed by $^1$H NMR and Mass Spectroscopy.

EXAMPLE 7

A mixture of 1.93 g of cyclohexylcarboguanamine, 3.5 g of dibutylcarbonate, and 12.0 g of sodium butoxide in n-butanol (20%) was heated at 90° C. for 30 minutes as in Example 5. Work-up of the reaction mixture gave a 3.6 gm of a crude product which contained N,N'-bis-butoxycarbonylcyclohexyl-carboguanamine as the major product as confirmed by its mass spectrum. Small amounts of the mono-carbamate were also formed.

EXAMPLE 8

12.5 g of acetoguanamine was placed in a 3-neck flask equipped with a rubber septum, a dropping funnel and a reflux condenser with an argon inlet. To it was added 51 ml of diethyl carbonate and the reaction flask heated in an oil bath at 90° C. 118 ml of 21% sodium ethoxide in ethanol was added through a dropping funnel over a period of 5 minutes. The reaction mixture was heated for 30 minutes. It was then cooled to room temperature and poured into 250 ml of 5% aq. Hcl. It was then extracted with $CH_2Cl_2$ (2×350 ml), the organic extract was washed with water (2×100 ml), dried over $Na_2SO_4$ and filtered. The filtrate was concentrated to dryness under reduced pressure to give 23 gm of crude N,N'-bis-ethoxycarbonyl-acetoguanamine. The structure was confirmed by mass spectroscopy.

EXAMPLE 9

The procedure of Example 8 was repeated with 1.93 g of cyclohexylcarboguanamine, 3.0 ml of diethylcarbonate and 9.3 ml of 21 % sodium ethoxide in ethanol to produce 3.1 g of crude N,N'-bis-ethoxylcarbonylcyclohexylcarboguanamine. The structure was confirmed by mass spectroscopy.

EXAMPLE 10

19.3 g of cyclohexylcarboguanamine was placed in a 3-neck flask equipped with a magnetic stirring bar, a rubber septum, a reflux condenser, an argon inlet and a dropping funnel. 20.2 ml of dimethylcarbonate was added to the reaction flask followed by slow addition of 55.0 ml of 25% sodium methoxide in methanol using a dropping funnel. The reaction mixture was stirred at room temperature for about an hour. The reaction flask contained a white precipitate at this stage. The reaction mixture was added, with stirring, to 400 ml of an ice-cold 5% aq. Hcl to completely dissolve the precipitate. The resulting solution was extracted with $CH_2Cl_2$ (2×250 ml), the organic layer was washed with water (2×100 ml), dried over $Na_2SO_4$, filtered and the solvent removed under reduced pressure to give 23.2 g of a residue containing mainly N,N'-bis-methoxycarbonyl-cyclohexylcarboguanamine as indicated by its mass spectrum.

EXAMPLE 11

The procedure of Example 8 was repeated with 1.87 g of benzoguanamine, 3.0 ml of diethylcarbonate, and 9.3 ml of 21% sodium ethoxide in ethanol to produce 2.95 gm of crude N,N'-bis-ethoxycarbonylbenzoguanamine as indicated by its mass spectrum.

EXAMPLE 12

18.7 g of benzoguanamine was allowed to react with 21.0 ml of dimethyl carbonate in the presence of 57.0 ml of 25% sodium methoxide solution in methanol at room temperature for nearly 6 hours. The addition of the reaction mixture to 300 ml of ice-cold 5% aq. Hcl resulted in the formation of a white precipitate which was filtered and washed with water. The filtrate was extracted with $CH_2Cl_2$ and the combined organic layer washed with water (2×200 ml), dried ($Na_2SO_4$) and filtered. The filtrate was concentrated under reduced pressure to remove the volatiles and the residue was treated with 300 ml of n-hexane/$CH_2Cl_2$ (10:1). A white precipitate was formed which was filtered, washed with n-hexane and dried. The product was identified by mass spectroscopy to be mainly N,N'-bis-methoxycarbonylbenzoguanamine.

EXAMPLE 13

25.0 g of acetoguanamine was reacted at room temperature with 40.4 ml of dimethylcarbonate in the presence of 110.0 ml of 25% sodium methoxide solution in methanol. After 2 hours at room temperature, the reaction mixture was added to 500 ml of ice-cold 5% aq. Hcl solution. It was extracted with $CH_2Cl_2$ (2×400 ml), the organic layer washed with water (2×100 ml), dried over $Na_2SO_4$, filtered and the solvent removed under reduced pressure. The crude product was stirred with 350 ml n-hexane for 2 hours at room temperature and the precipitate formed was filtered, washed with n-hexane and dried under reduced pressure to give 16 g of a product identified by $^1$H and $^{13}$C NMR and mass spectroscopy to be N,N'-bis-methoxycarbonylacetoguanamine.

EXAMPLE 14

A slurry of melamine (0.622 g, 0.0049 mol) and dry dimethyl carbonate (1.42 g, 0.17 mol) was heated to 90° C. under a dry argon blanket. A 20% solution of sodium n-butoxide in butanol (5.5 g, 0.01 mol of sodium n-butoxide) was added to the slurry at 90° C.

Heating was continued for four hours. The reaction mixture was acidified and extracted with methylene chloride. The methylene chloride layer was concentrated under reduced pressure to afford the product. HPLC and mass spectral analysis of the reaction mixture showed that it contained a mixture of tris-carbamate products: 2,4,6-tris-butoxycarbonylamino-1,3,5-triazine, 2,4-bis-butoxycarbonylamino-6-methoxycarbonylamino-1,3,5-triazine, and 2-butoxycarbonylamino-4,6-bis-methoxycarbonylamino-1,3,5-triazine.

EXAMPLE 15

Sodium metal (32 g, 1.39 mol) was slowly dissolved in sec-butyl alcohol (3101 g, 41.9 mol) to form a 4.25% alkoxide solution which was then heated to 90° C. under argon blanket. Dimethyl carbonate (65 g, 0.7 mol) and melamine (24.12 g, 0.19 mol) were then added to the hot alkoxide solution quickly in succession. The contents in the flask were heated for 135 minutes. Upon cooling the reaction mixture was acidified and extracted with methylene chloride. The methylene chloride layer was dried and then concentrated under reduced pressure to afford 70 g (86% yield) of mainly 2,4,6-tris-sec-butoxycarbonylamino-1,3,5-triazine as indicated by $^1$H NMR.

EXAMPLE 16

A slurry of 1.0 g of melamine in 3.8 g of a 20 wt. % solution of sodium butoxide in butanol was heated to 90° C. under argon, with stirring. 4.26 g dibutyl carbonate total was added in three equal portions at 15 minute intervals. After maintaining the mixture at 90° C. for an additional 30 minutes, it was cooled to room temperature and 16 ml of methylene chloride and 8 ml of 2N sulfuric acid were added. The organic phase was concentrated under reduced pressure. The resulting solids were shown to be a primarily 2,4,6-tris-butoxycarbonylamino-1,3,5-triazine with a small amount of 2-amino-4,6-bis-butoxycarbonylmino-1,3,5-triazine by $^1$H NMR. Overall yield of tris product was about 13%.

EXAMPLE 17

To a slurry of 2.0 g of melamine in 9.1 g of dibutylcarbonate was added 27.5 g of a 20 wt. % solution of sodium butoxide in butanol. The mixture was stirred at room temperature for 2 hours. The reaction mixture was acidified by addition of 30 ml of 2N sulfuric acid and 30 ml of methylene chloride. The salts were filtered and the layers separated. The organic layer was dried over anhydrous sodium sulfate and the concentrated under reduced pressure. The product contained primarily 2-amino-4,6-bisbutoxycarbonylamino-1,3,5-triazine and 2,4,6-trisbutoxycarbonylamino-1,3,5-triazine by TLC and $^1$H NMR analysis.

EXAMPLE 18

Potassium hydroxide was dissolved in butanol. Water and butanol were removed by distillation at 125° C. using a Dean-Stark trap. The resulting solution was diluted with butanol and octane. Additional water was removed by azeotropic distillation and the final solution was dried over 3A molecular sieves. The solution was diluted with butanol to 10 wt % on a potassium butoxide basis. A slurry of 2.0 g melamine in 11.6 g dibutyl carbonate was heated to 90° C. under nitrogen, with stirring, and 64.1 g of the potassium butoxide solution was added. After maintaining the mixture at 90° C. for an additional 60 minutes, it was cooled to room temperature and 50 ml of methylene chloride and 30 ml of 2N sulfuric acid were added. The phases were separated and the organic phase concentrated under reduced pressure. The resulting solid was shown to be a mixture of 2-amino-4,6-bis-butylcarbonylamino-1,3,5-triazine and 2,4,6-tris-butoxycarbonylamino-1,3,5-triazine by $^1$H NMR.

EXAMPLE 19

Sodium metal (21.5 g, 0.93 mol) was slowly dissolved in isopropyl alcohol (709.5 g, 11.7 mol) to form a 10% solution, which was then heated to 90° C. under a dry argon blanket. 2,4,6-tris-butoxycarbonylamino-1,3,5-triazine (49.6 g, 0.116 mol) was added to the alkoxide solution at 90° C. The contents in the flask were heated for 30 minutes. Acidification followed by extraction with methylene chloride led to 34 g (76% yield) of product. The product was identified to be a 50-50-mixture of the isopropyl-and butyl-tris carbamates by $^1$H NMR.

EXAMPLE 20

Sodium metal (0.9 g, 0.039 mol) was slowly dissolved in 2-ethylhexyl alcohol (34.4 g, 0.265 mol) to form a 16.8% alkoxide solution which was then heated to 90° C. under argon blanket. Dimethyl carbonate (0.69 g, 0.007 mol) and melamine (0.2343 g, 0.178 mol) were then added to the hot alkoxide solution quickly in succession. The contents in the flask were heated for 16 hours.

Upon cooling the reaction mixture was acidified and extracted with methylene chloride. The methylene chloride layer was concentrated under reduced pressure to give 0.4133 g (38% yield) of a mixture of methyl and 2-ethylhexyl derivatives in which the bis- to tris-mole ratio was found to be 1:1 by $^1$H NMR spectroscopy.

EXAMPLE 21

A slurry of melamine (0.622 g, 0.005 mol) and butylchloroformate (2.5 g, 0.18 mol) was placed under a dry argon blanket. A 20% solution of sodium n-butoxide in butanol (10.8 g, 0.02 mol of sodium n-butoxide) was added to the slurry. The temperature was raised and maintained at 90° C. for 2 hours.

At the end of the two hour period, the mixture was cooled and poured into a methylene chloride (50 ml)/2N sulfuric acid (25 ml) mixture. The methylene chloride layer was washed with saturated sodium chloride solution, dried over magnesium sulfate and concentrated under reduced pressure to yield 73.1 mg (12.5%) of a product identified to be 2,4,6-tris-butoxycarbonylamino-1,3,5-triazine by $^1$H NMR spectroscopy.

EXAMPLE 22

A mixture of sodium butyl carbonate (2.52 g, 18 mmol, prepared from butanol, sodium metal, and carbon dioxide), 10 ml of anhydrous dimethyl formamide, Aliquat 336 (0.15 g, 0.4 mmol), and 1-bromobutane (2.8 g, 20.5 mmol) was charged to a 50 ml reaction flask and heated under a carbon dioxide atmosphere at 85° C. for six hours. Gas chromatographic analysis of the mixture after four hours showed that dibutylcarbonate had been formed in-situ. The reaction mixture was then cooled to room temperature and the system was flushed with nitrogen. Melamine (0.50 g, 4 mmol) and sodium hydride (0.31 g, 12.9 mmol) were then added and the resulting slurry was heated again to 85° C. with stirring for 3 hours. The mixture was then cooled and the insolubles were filtered off. Concentration of the filtrate under reduced pressure afforded 1.05 g of a yellow solid which, by mass spectrum analysis, contained 2,4,6-tris (butoxycarbonylamino)-1,3,5-triazine along with some 2,4-bis(butoxy-carbonylamino)-6-amino-1,3,5-triazine.

Although the present invention has been described with reference to certain preferred embodiments, it is apparent that modification and variations thereof may be made by those skilled in the art without departing from the scope of this invention as defined by the appended claims.

We claim:

1. A substantially halogen contamination free crosslinker composition comprising a carbamate functional 1,3,5-triazine of the general formula:

wherein

Z' is selected from the group consisting of hydrogen, hydrocarbyl and a group represented by the formula NHQ', each Q' is independently selected from the group consisting of a hydrocarbyl, a hydrocarbyloxy hydrocarbyl and a group represented by the formula COOY, with the proviso that a least two of the Q' groups are COOY, and each Y is independently a hydrocarbyl group or a hydrocarbyloxy hydrocarbyl ether group.

2. The substantially halogen contamination free crosslinker composition of claim 1, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

3. The substantially halogen contamination free crosslinker composition of claim 2, wherein each Y is independently an alkyl of 1 to 4 carbon atoms.

4. The substantially halogen contamination free crosslinker composition of claim 3, wherein each Y is independently methyl or butyl, with the proviso that at least one Y is butyl.

5. The substantially halogen contamination free crosslinker composition of claim 1, wherein Z' is selected from the group consisting of hydrogen and hydrocarbyl.

6. The substantially halogen contamination free crosslinker composition of claim 5, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

7. The substantially halogen contamination free crosslinker composition of claim 6, wherein each Y is independently an alkyl of 1 to 4 carbon atoms.

8. The substantially halogen contamination free crosslinker composition of claim 7, wherein each Y is independently methyl or butyl, with the proviso that at least one Y is butyl.

9. The substantially halogen contamination free crosslinker composition of claim 1, wherein Z' is a group represented by the formula NHQ'.

10. The substantially halogen contamination free crosslinker composition of claim 9, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

11. The substantially halogen contamination free crosslinker composition of claim 10, wherein each Y is independently an alkyl of 1 to 4 carbon atoms.

12. The substantially halogen contamination free crosslinker composition of claim 11, wherein each Y is independently methyl or butyl, with the proviso that at least one Y is butyl.

13. The substantially halogen contamination free crosslinker composition of claim 9, wherein each Q' is a group COOY.

14. The substantially halogen contamination free crosslinker composition of claim 13, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

15. The substantially halogen contamination free crosslinker composition of claim 14, wherein each Y is independently an alkyl of 1 to 4 carbon atoms.

16. The substantially halogen contamination free crosslinker composition of claim 15, wherein each Y is independently methyl or butyl, with the proviso that at least one Y is butyl.

17. A curable composition comprising a crosslinker and a composition capable of reacting therewith, wherein the crosslinker comprises a substantially halogen contamination free crosslinker composition comprising a carbamate functional 1,3,5-triazine of the general formula:

wherein
Z' is selected from the group consisting of hydrogen, hydrocarbyl, and a group represented by the formula NHQ',
each Q' is independently selected from the group consisting of a hydrocarbyl, a hydrocarbyloxy hydrocarbyl and a group represented by the formula COOY, with the proviso that a least two of the Q' groups are COOY, and
each Y is independently a hydrocarbyl group or a hydrocarbyloxy hydrocarbyl ether group.

18. The curable composition of claim 17, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

19. The curable composition of claim 18, wherein each Y is independently an alkyl of 1 to 4 carbon atoms.

20. The curable composition of claim 19, wherein each Y is independently methyl or butyl, with the proviso that at least one Y is butyl.

21. The curable composition of claim 17, wherein Z' is selected from the group consisting of hydrogen and hydrocarbyl, and each Q' is a group COOY.

22. The curable composition of claim 21, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

23. The curable composition of claim 22, wherein each Y is independently an alkyl of 1 to 4 carbon atoms.

24. The curable composition of claim 23, wherein each Y is independently methyl or butyl, with the proviso that at least one Y is butyl.

25. The curable composition of claim 17, wherein Z' is a group represented by the formula NHQ'.

26. The curable composition of claim 25, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

27. The curable composition of claim 26, wherein each Y is independently an alkyl of 1 to 4 carbon atoms.

28. The curable composition of claim 27, wherein each Y is independently methyl or butyl, with the proviso that at least one Y is butyl.

29. The curable composition of claim 25, wherein each Q' is a group COOY.

30. The curable composition of claim 29, wherein each Y is independently selected from the group consisting of an alkyl of 1 to 20 carbon atoms; an alkenyl of 3 to 20 carbon atoms; an aryl of 6 to 20 carbon atoms; an aralkyl of 7 to 20 carbon atoms; and a hydrocarbyloxy hydrocarbyl ether group wherein both hydrocarbyl portions are selected from an alkyl of 1 to 20 carbon atoms, an alkenyl of 3 to 20 carbon atoms, an aryl of 6 to 20 carbon atoms and an aralkyl of 7 to 20 carbon atoms.

31. The curable composition of claim 30, wherein each Y is independently an alkyl of 1 to 4 carbon atoms.

32. The curable composition of claim 31, wherein each Y is independently methyl or butyl, with the proviso that at least one Y is butyl.

* * * * *